(12) United States Patent
Thomsen

(10) Patent No.: US 12,029,885 B2
(45) Date of Patent: Jul. 9, 2024

(54) PROTECTIVE CAP FOR A DEVICE

(71) Applicant: IN.TOOL ApS, Holte (DK)

(72) Inventor: Jakob Dahl Thomsen, Holte (DK)

( * ) Notice: Subject to any disclaimer, the term of this patent is extended or adjusted under 35 U.S.C. 154(b) by 0 days.

(21) Appl. No.: 14/442,504

(22) PCT Filed: Nov. 13, 2013

(86) PCT No.: PCT/DK2013/050375
§ 371 (c)(1),
(2) Date: May 13, 2015

(87) PCT Pub. No.: WO2014/075685
PCT Pub. Date: May 22, 2014

(65) Prior Publication Data
US 2016/0271336 A1   Sep. 22, 2016

Related U.S. Application Data

(60) Provisional application No. 61/738,478, filed on Dec. 18, 2012.

(30) Foreign Application Priority Data

Nov. 13, 2012 (DK) .......................... PA 2012 70698
Feb. 27, 2013 (DK) .......................... PA 2013 70116
Sep. 20, 2013 (DK) .......................... PA 2013 70527

(51) Int. Cl.
*A61M 5/32*     (2006.01)
*A61B 5/15*     (2006.01)
(Continued)

(52) U.S. Cl.
CPC ..... *A61M 5/3202* (2013.01); *A61B 5/150633* (2013.01); *A61B 5/150717* (2013.01);
(Continued)

(58) Field of Classification Search
CPC .............. A61M 5/3202; A61M 5/3137; A61M 5/31568; A61M 5/3213; A61M 5/20; A61M 2005/312; A61M 5/178; A61M 5/28; A61M 2205/3592; A61M 2205/583; A61M 2205/587; A61M 2205/8206; A61M 5/3204; A61M 5/321; A61M 5/3216;
(Continued)

(56) References Cited

U.S. PATENT DOCUMENTS 4,085,737 A * 4/1978 Bordow ............. A61B 5/15003
                                                              600/576
5,135,508 A    8/1992 Vernamonti
(Continued)

FOREIGN PATENT DOCUMENTS

DE          19821934       11/1999
WO      WO-1997/10866       3/1997
(Continued)

*Primary Examiner* — Emily L Schmidt
*Assistant Examiner* — Alexandra Lalonde

(57) ABSTRACT

The invention regards a protective cap for a delivery system, said cap comprising a tip part releasably attached to a main part, wherein the tip part and the main part together form an elongated body with a closed tip end, and the main part comprises at least one means for assisting the use of the delivery system.

15 Claims, 21 Drawing Sheets

(51) Int. Cl.
*A61M 5/31* (2006.01)
*A61M 5/315* (2006.01)
*A61M 5/42* (2006.01)

(52) U.S. Cl.
CPC .... *A61B 5/150824* (2013.01); *A61B 5/15087* (2013.01); *A61M 5/3137* (2013.01); *A61M 5/31568* (2013.01); *A61M 5/321* (2013.01); *A61M 5/427* (2013.01); *A61M 2005/3139* (2013.01); *A61M 2205/3569* (2013.01); *A61M 2205/3592* (2013.01); *A61M 2205/502* (2013.01); *A61M 2205/583* (2013.01); *A61M 2205/587* (2013.01); *A61M 2205/8206* (2013.01)

(58) Field of Classification Search
CPC ...... A61M 5/3219; A61M 5/002; A61M 5/34; A61M 5/343; A61M 5/344; A61M 5/345; A61M 5/346; A61M 5/347; A61M 5/348; A61M 2005/3215; A61M 2005/3217; A61M 2005/3104; A61M 2005/3109; A61M 2005/3106; A61M 2005/3103; A61B 5/150633; A61B 5/150717; A61B 5/150824; A61B 5/150847; A61B 5/14532; A61J 7/0436
See application file for complete search history.

(56) References Cited

U.S. PATENT DOCUMENTS

| | | | | |
|---|---|---|---|---|
| 5,607,400 A * | 3/1997 | Thibault | ............ | A61M 5/31513 604/218 |
| 5,681,295 A * | 10/1997 | Gyure | ................ | A61M 5/3202 604/192 |
| 6,482,185 B1 * | 11/2002 | Hartmann | ......... | A61M 5/31525 604/189 |
| 7,771,397 B1 | 8/2010 | Olson | | |
| 2002/0193737 A1 * | 12/2002 | Popovsky | ............. | A61M 5/326 604/110 |
| 2004/0062148 A1 * | 4/2004 | Skyggebjerg | ......... | A61M 5/178 368/107 |
| 2004/0236284 A1 * | 11/2004 | Hoste | .................... | A61M 5/326 604/198 |
| 2005/0148932 A1 * | 7/2005 | Rimlinger | ......... | A61M 5/31501 604/110 |
| 2005/0171484 A1 | 8/2005 | Jangula | | |
| 2006/0247583 A1 * | 11/2006 | Klint | ..................... | A61M 5/329 604/264 |
| 2006/0258991 A1 | 11/2006 | Lin | | |
| 2007/0179451 A1 * | 8/2007 | Sprinkle | ............. | A61M 5/3216 604/192 |
| 2008/0228147 A1 * | 9/2008 | David-Hegerich | ... | A61M 5/326 604/198 |
| 2009/0312714 A1 * | 12/2009 | Martinsson | ......... | A61M 5/3134 604/197 |
| 2010/0010454 A1 * | 1/2010 | Marshall | ............. | A61M 5/2033 604/208 |
| 2010/0249748 A1 * | 9/2010 | Szucs | .................... | A61M 5/326 604/506 |
| 2010/0256486 A1 * | 10/2010 | Savage | .................. | A61M 5/007 600/432 |
| 2012/0095438 A1 * | 4/2012 | Lanin | .................. | A61M 5/3137 604/506 |
| 2012/0225405 A1 * | 9/2012 | Boehm | ............... | B29C 45/0013 433/90 |
| 2012/0283647 A1 * | 11/2012 | Cronenberg | ...... | A61M 5/31535 604/207 |
| 2012/0330228 A1 * | 12/2012 | Day | .................. | A61M 5/14244 604/82 |
| 2013/0138040 A1 * | 5/2013 | Weinandy | ............... | A61M 5/24 604/111 |
| 2013/0310756 A1 * | 11/2013 | Whalley | ................. | A61M 5/31 604/189 |

FOREIGN PATENT DOCUMENTS

| | | | | |
|---|---|---|---|---|
| WO | WO-2002/087670 | 11/2002 | | |
| WO | WO-2012/103141 | 8/2012 | | |
| WO | WO 2012164397 A1 * | 12/2012 | ............. | A61M 5/20 |
| WO | WO-2013/056714 | 4/2013 | | |

* cited by examiner 1a　　　1b

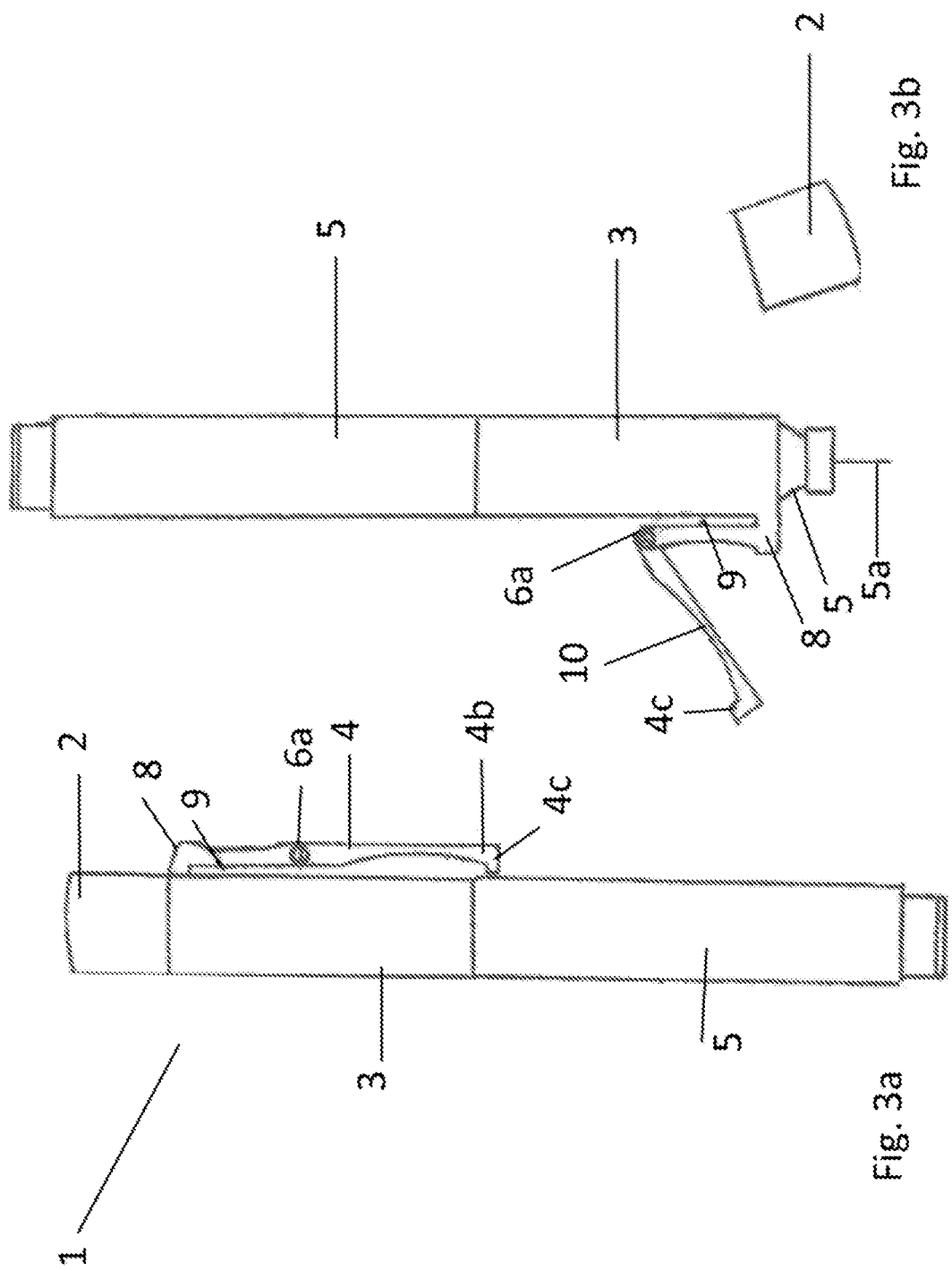

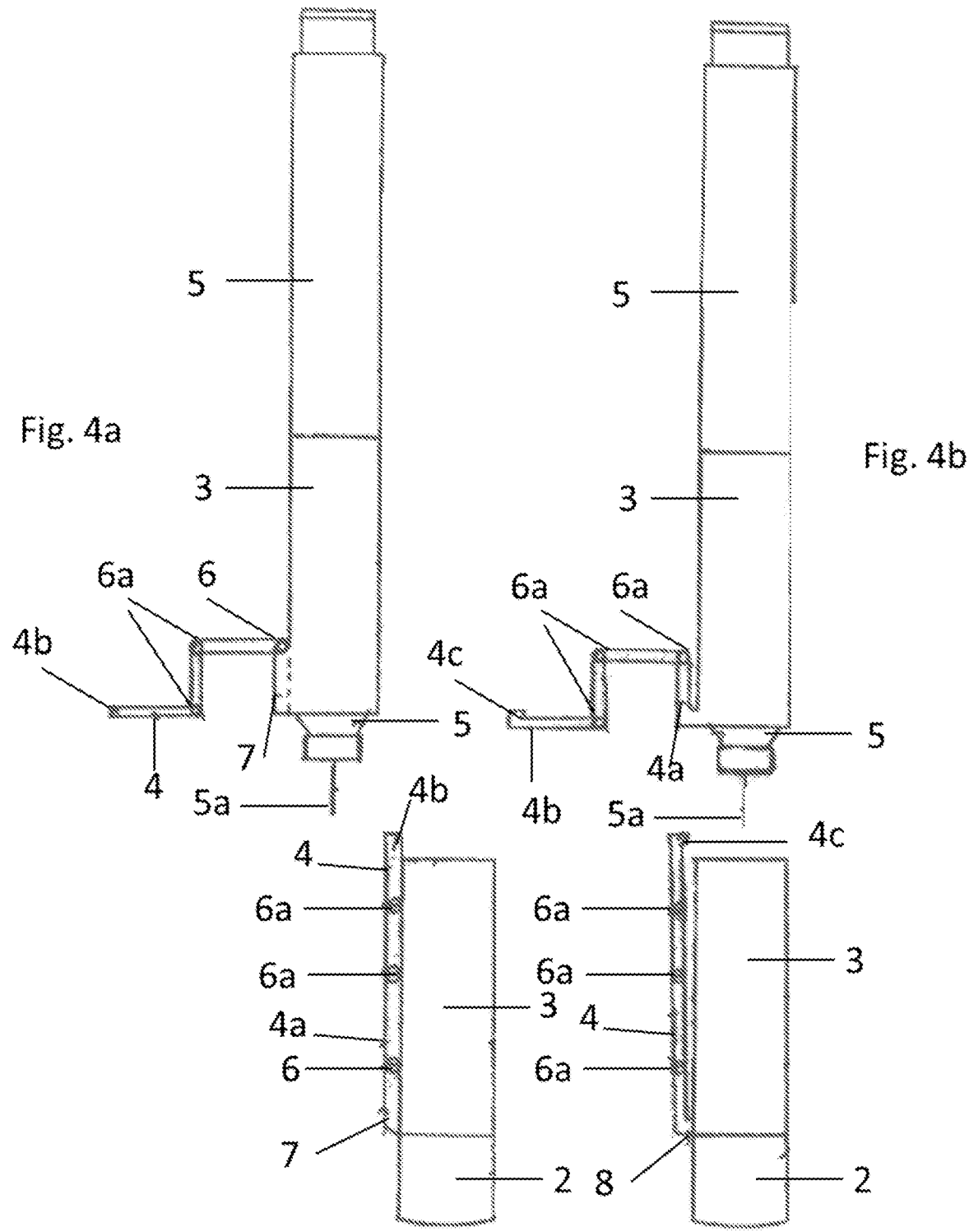

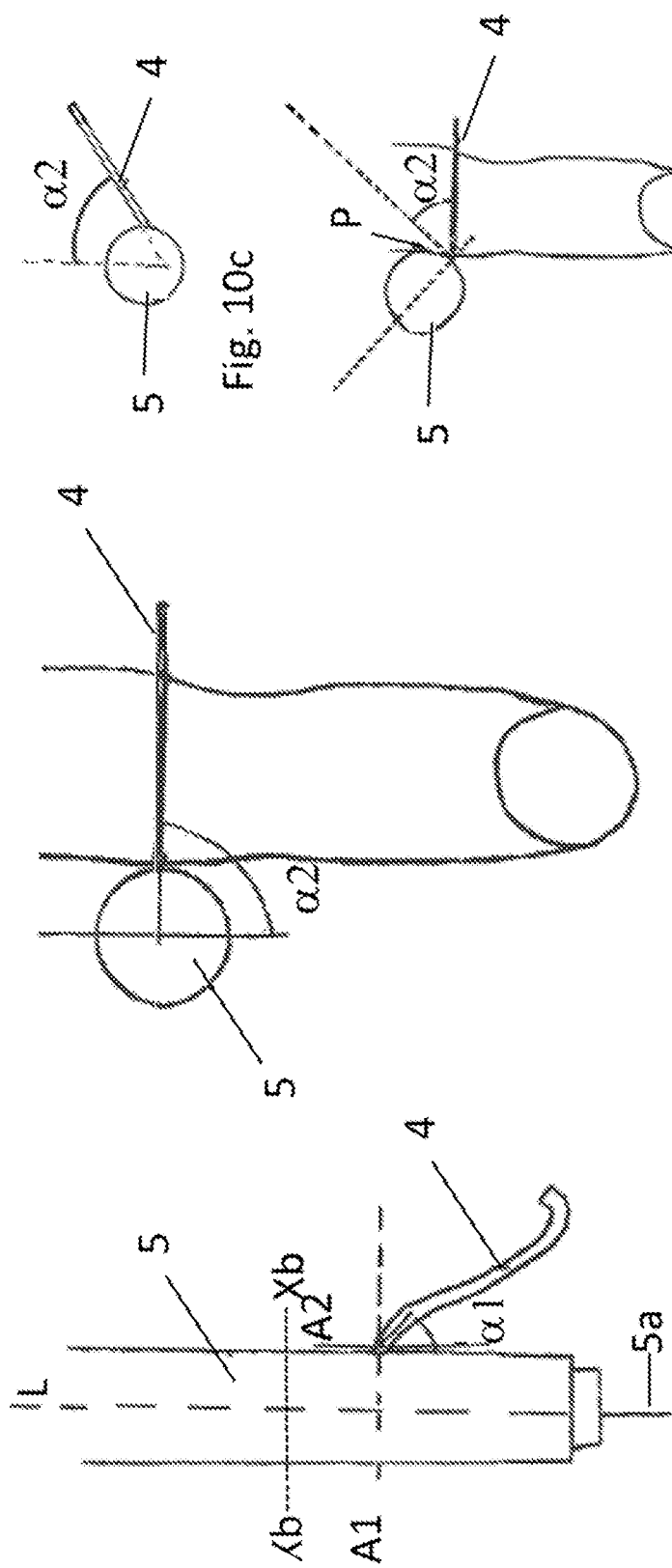

FIG. 16
16a
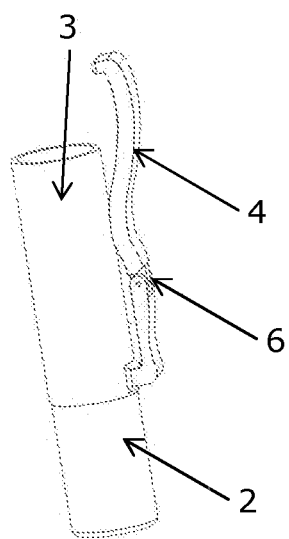
16b
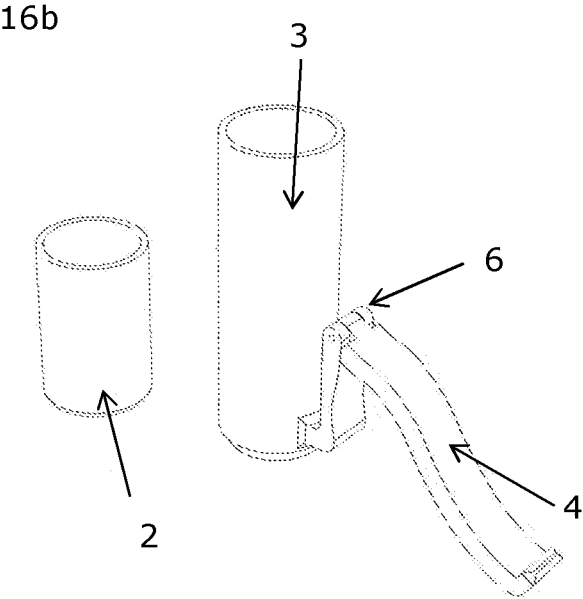

16c

PROTECTIVE CAP FOR A DEVICE

SUMMARY OF THE INVENTION

The invention relates to a device which can assist the user of e.g. a delivery system during injection.

BACKGROUND OF INVENTION

It is well known that a number of users of delivery systems such as insulin pens or syringes are performing their injections incorrectly (not in full compliance with given instructions) and some are afraid of the injections (needle fear). Improvements regarding the function of delivery systems are needed to improve the quality of the injections and increase the adherence of the users to the treatment plans given by authorized health personal thus increasing the efficiency of the treatment. Users of delivery systems such as insulin or glucagon-like peptide-1 (GLP-1) pens or syringes often need to perform injections where there is no light or too little light to be able to see the skin and choose a suitable injection site. Also many users of injector pens face problems due to a lack of control or reduced control of the injection means leading to discomfort due to vibrations of hands and delivery system during use.

The user of a delivery system such as an insulin pen or a syringe needs to find an appropriate injection site and to ensure a suitable angle between the skin at the injection site and the needle of the delivery system depending on both the injection site and the length of the needle. Additionally the user needs to control the depth of the injection which depends on the injection site and/or the substance to be injected. Furthermore, depending on the substance to be injected, injection in blood veins or small blood capillaries is either to be avoided or is preferred, thus the user needs to be attentive to the location of blood veins or small blood capillaries. In other words it is desired that the user is in control of the delivery system.

However, means for ensuring sufficient light during injection or for helping the user gain or improve control during injection do not exist as add-ons to delivery systems in a form where they are readily portable and easy to bring along, for example incorporated into or attached to the delivery system.

Thus, there is a need for devices which can assist users of various devices incl. delivery systems to improve their use of said device.

SUMMARY OF INVENTION

Therefore, in a first aspect of the present invention is provided a protective cap which can assist the user of a device during use of said device.

In a second aspect of the present invention is provided a protective cap which can help stabilize a device during use.

In a third aspect of the present invention is provided a protective cap which provides improved lighting conditions during use.

These and other advantages are provided by a protective cap for a device, said cap comprising a tip part releasably attached to a main part wherein the tip part and the main part together form an elongated body with a closed tip end, and the main part comprises at least one means for assisting the use of the device. The main part may consist of two parts: an inner part and an outer part. A protective cap with a tip part releasably attached to a main part allows the user to remove the tip part from the main part while leaving the main cap part attached to the device. When the main part comprises at least one means for assisting the use of the device, the main part can be used to attach the at least one means for assisting the use of the device to the device. The at least one means for assisting the use of the device can be attached to the device by the main part and the tip part can be removed to gain access to an active part of the device, thereby enabling the use of the device while the main cap part is still attached to the device.

The fact that the tip part of the protective cap can be released from the main part of the protective part means that the main part can be kept at the delivery system/device allowing for the use of the assisting means attached to or integrated into the main cap.

The fact that the protective cap of the device is used to provide the assisting means has the big advantage that the assisting means are brought along together with the device, i.e. when the protective cap in this way is provided with means for assisting the use of the device, it is possible to keep the means for assisting the use together with the device at all times in order to avoid forgetting the assisting means or having to bring the assisting means along as a separate part.

The fact that the protective cap with its tip part can be released from the delivery system (or other device) in one unit (the tip part and main cap part attached to each other) means that the delivery system (or other device) can be used without the assisting means provided by the protective cap. The delivery system can, if the user so prefers, be used as has traditionally been the case. There are no drawbacks to the user as the means for assisting does not need to occupy much, if any, additional space and does not affect the functionality of the delivery system if not used. Another advantage of the releasable protective cap is of a financial order: the protective cap may be reused with different injection devices, some of which are disposable, thus the user does not need to buy several protective caps to use with several devices.

Thus, the protective cap according to the present invention can be used as an alternative to existing traditional protective caps. If the user does not want to use the assisting means, the entire protective cap can be removed from the device during use. Similar to several traditional protective caps, the present protective cap when attached to the injection device can give the impression that the injection device is a pen, thereby allowing the user to discretely carry the injection device.

The device can for example be an injector pen or a delivery system. For example if the device is a delivery system such as an injector pen or a syringe with a needle, the tip part can be removed to gain access to the needle while at least one means for assisting the use of the device is attached to the delivery system by the main cap part still attached to the delivery system. For example the delivery system is for delivering a medical substance such as insulin.

If the protective cap is arranged to allow use of the delivery system when the main part of the protective cap is mounted on the delivery system and the tip part is released from the main part a simple assisting device is achieved.

The protective cap can comprise means for clicking or otherwise releasably locking onto the device.

The protective cap can advantageously have a shape similar to that of traditional protective caps for devices such as for example delivery systems.

The main part may consist of an inner part and an outer part. The outer part may cover both the inner part of the main cap and the tip part, or it may cover the inner part of the main cap only. The outer part and/or the inner part may comprise means allowing the outer part to releasably lock on the inner part. The assisting means may be located on the outer part or on the inner part. Where the assisting means are located when the main part consists of an inner part and an outer part may depend on the function of the assisting means. The outer part of the main part may comprise assisting means.

In several embodiments the tip part and the main part together form a substantially tubular body as this is a shape which may fit pens, delivery systems and injectors.

In advantageous embodiments the means for assisting the device such as a delivery system is a grip unit on one of the sides of the main part of the protective cap arranged to be engaged by the first hand of a user while the delivery system is activated by the second hand of the user This means that by using the present invention coordination of the two hands during injection is made easier. This is achieved in that the first hand holds the grip, and thereby supports the delivery device during the injection. Hereby, the instrument helps stabilize the delivery system during injection and thus helps keep the delivery system steady even during activation of the delivery system and during the time it takes for the injection to take place.

Thus, the present invention may help avoid the problems occurring when the second hand is holding and activating the delivery system without any support and vibrations generated in connection with the injection are transmitted to the needle in the skin. The vibrations occur partly because of the pressure of the fingers to the release button of the delivery system (as the thin needle does not meet any significant resistance under the skin), and partly due to the fact that the hand which carries out the injection primarily is controlled by the strong wrist and arm muscles which are not suitable for precise control of the small movements required for injection of medicine.

The grip unit may be any suitable unit adapted for providing a grip by using one finger, two fingers or several fingers.

The length of the grip may be adapted to suit the intended use—e.g. the use of a user with a small hand or a large hand. Thus e.g. the grip may be between 3 and 8 cm or even between 2 and 12 cm to suit specific hand positions during use or even enable a grip suited for children.

Hereby, the protective cap according to the invention makes it possible to assist and facilitate the calm and controlled hand movements that are preferred during subcutaneous injection. The effect from shaking hands during the delivering of a medication from an injector can be reduced by using the protective cap with a grip unit according to the invention.

If the delivery system is an insulin injector or e.g. a syringe, the present invention can be applied with great advantages. The insulin injection takes time which requires that the user holds the delivery system steady during this time, which can be a straining or even impossible task depending on the physical ability of the user and also e.g. of the place of the injection site on the user body. When the instrument of the present invention is used, the user is using both hands—one hand holding the grip unit supported by the body and another hand activating the delivery device and holding it during the time it takes to perform the injection. This means that instead of having a passive first hand as is the case without the present invention, now the first hand is active in the process of supporting the delivery system.

In some preferred embodiments the grip unit is comprised by a folding clip on said main cap part. In several embodiments, the clip is configured to form a grip during use of the delivery system, which grip is arranged to engage with a first hand of a user providing stability to the delivery system during injection, and the main cap part is configured to attach the grip to the delivery system during use. If the grip is also a clip, it can when unfolded be used to fasten the delivery device in e.g. a pocket when not in use.

In other embodiments, other means for assisting the delivery systems may be at least one O-ring, such as two O-rings, on one of the sides of the main part of the protective cap arranged to be engaged by the first hand of a user while the delivery system is activated by the second hand of the user. The at least one O-ring may assist the user by providing him with a better grip on the main part. The at least one O-ring should be such that it is possible to pass a finger through. Because O-rings are generally flexible, they can accommodate many sizes of fingers. In some embodiments, the at least one O-ring is attached to the main part by methods known in the art. Thus in some embodiments it may be glued or attached by ultrasonic or laser welding In some embodiments the at least one O-ring is two O-rings arranged on opposite sides of the main part of the protective cap. The two O-rings may be arranged symmetrically, i.e. at the same height on the main part of the protective cap. Alternatively, the two O-rings are not at the same height on the main part of the protective cap. It is of importance that the two O-rings are arranged such that they allow the user to pass one finger through each O-ring. Thus in the case where the two O-rings are not arranged symmetrically, they shall be arranged so that it is possible and preferably convenient for the user to pass two fingers through the two rings and hold the main part in a stable manner.

In other embodiments, the means for assisting the delivery system is at least one recess, such as two recesses, such as three recesses, such as four recesses, such as five recesses, such as six recesses, located on the main part of the protective cap. In some embodiments, the at least one recess is circular, (FIG. 19) and runs around the circumference of the main part or partly runs around in order to allow for the proper use of a finger grip and/or the traditional clip of the device. In such embodiments, the user may hold the main part anywhere on the side, whereby the recess will prevent his or hers fingers from gliding. The at least one recess may be at least two recesses, such as three recesses. In these embodiments, the recesses should be located far enough from each other on the main part of the protective cap to allow the user to position his or hers fingers between them. The use of three recesses allows the user to position two fingers at different vertical positions on the main part, thereby not only preventing his fingers from gliding but also securing his/her hold on the main part and giving the user a better view of the needle.

In another embodiment, the at least one recess is a pair of recesses, wherein the recesses are protuberances located on discrete locations on the side of the main part. The at least one recess may be one pair of recesses, two pairs of recesses, three pairs of recesses. The two recesses of each pair should then be arranged so that they are, even if not necessarily symmetrical, essentially on opposite sides of the main part, so as to prevent the user's fingers from gliding when the user holds the main part with two fingers. In embodiments with two or three pairs of recesses, the pairs should be located far enough from each other on the main part of the protective cap to allow the user to position his or her fingers between them. The use of three pairs of recesses allows the user to position two fingers at different vertical positions on the main part, thereby not only preventing his/her fingers from gliding but also securing his/her hold on the main part and giving the user a better view of the needle.

When the means for assisting delivery enable a more secure hold of the main part as described above, and the main part consists of an inner part and an outer part, such means are preferably located on the outer part.

In further embodiments, the means for assisting delivery is a combination of at least one O-ring, and/or at least one recess, and/or a grip.

In other advantageous embodiments, the means for assisting the delivery system is a light source which can light up an area around the device thereby assisting the user. For example, the device can be an insulin pen and the light source will enable the user to see the area of the skin to select an appropriate are for making an injection of the insulin. In some embodiments, the light source is a white, a red or a near-infrared light source. The light source allowing enhanced visualisation of the area of injection may be a near-infrared light source, since this kind of light source is not followed by emission of heat which can be uncomfortable for the user. Light sources allowing enhanced visualisation of veins may also be used. The light source allowing enhanced visualisation of veins may also be a green or blue light source.

In other embodiments, the present invention provides a protective cap further comprising a timer with a display. The timer can show the time elapsed since the last injection of medicine, thus allowing the user to better keep records of his medicine usage without having to remember the timer of the last injection or without having to use additional means such as a notebook. The timer may be located in various positions of the protective cap. For example it may be placed on the top of the protective cap (the tip part), or on its side. In other embodiments, the timer is located on the side of the main cap. The display can show the time as absolute time values (in hours, minutes and seconds). For the injection of some medicines/substances precision as to time is not an absolute requirement; thus the display may also show the time since the last injection as time intervals: the time may be rounded to the closest full minutes, or the closest 15 or 30 seconds. In other embodiments, time elapsed may be visualised as a shape being gradually greyed out on the display, such as a circle or a bar, where the greyed out area is proportional to the time elapsed since the last injection.

In some embodiments, the time display is located on the top of the tip part, and displaying time is achieved by LED diodes which gradually light up a circular shape. In other embodiments, the time display gives the time with a precision of the order of one minute during the first half hour or during the first hour after injection. In some embodiments, after the first hour and for at least 12 hours, such as 12 hours, such as 14 hours, such as 16 hours, such as 18 hours, such as 20 hours, such as 22 hours, such as 24 hours, each new hour is displayed with a precision of one hour.

In some embodiments, the timer is automatically activated upon separation of the tip part and the main part of the protective cap. In other embodiments, the timer is automatically activated upon separation of the main part from the delivery system. In advantageous embodiments, activation requires that separation of the tip part and the main part lasts longer than a specific duration. Such embodiments allow the user to demonstrate the use of his injection device to others without doing an injection and activating the timer, or the user may change his mind and decide to postpone the injection without activating the timer. In some embodiments the specific duration is determined by the user. In other embodiments the specific duration is specified by the manufacturer. For example, the specific duration may be 10 or 15 seconds.

In other embodiments, the protective cap further comprises means for resetting the timer to the previous value. This can be advantageous if the user has to separate the tip part and the main part for a duration which automatically activates the timer, for example if the user made a mistake, changed his mind, or wanted to demonstrate all the features of his injection device. In some embodiments, the means for resetting the timer to the previous value is a button, which may be activated by the user. In other embodiments, the user can reset the timer by quickly releasing the tip part from the main part more than once within a short interval, such as twice within 10 seconds.

In some embodiments the protective cap further comprises a battery. The battery may provide the timer and/or the light source—or any other assisting mean/tool requiring electricity—with energy.

The timer may advantageously be combined with the light source. For example in some embodiments, the timer and a first battery are placed on the top of the tip part of the protective cap. In other embodiments, the timer and a first battery are placed on the tip part of the protective cap, and the light source and a second battery are placed on the main part of the protective cap. In other, preferred embodiments, in order to reduce the volume of the tip part, the timer and the battery are placed on the tip part, the main part and the tip part are connected by a conducting contact point allowing charging of a secondary source of energy placed in the main part or vice versa. By conducting contact point is understood a connexion allowing electricity to be conducted between the main part and the tip part. Upon separation of the tip part and the main part, the secondary energy source has stored enough energy to allow the light source to function independently of the battery for a duration long enough to allow injection.

The protective cap may also comprise means of visualising the number of medicine units injected at the last injection. Such means may be a digital display, the number of units being entered by the user, or it may be a rotating disc with numbers, where the user rotates the disc until the relevant number is displayed. In some embodiments, the means for visualising the number of injected units is placed next to the timer. In alternative embodiments, the timer display can be switched to show the number of injected units.

In other embodiments, the protective cap further comprises means for transmission of data. The data to be transmitted may be any data relevant to the user and can in some embodiments be specified by the user. For examples, relevant data may be the time since the last injection and/or the amount of injected units. In some embodiments, the means for transmitting the data are capable of communicating wirelessly with a receiving device. In advantageous embodiments, the receiving device is a smartphone or a Blood Glucose Monitoring Device. Transmission may occur via wireless technologies known in the art, including, but not limited to: Bluetooth, Bluetooth low energy (BLE), near field communication (NFC) or radio frequency identification (RFID). Such embodiments are particularly interesting because it makes it unnecessary to include a display on the protective cap, thus simplifying the cap. In addition it is practical for users who carry a smartphone but perhaps prefer not to carry the injection device or the protective cap at all times. Moreover it allows for automatic inclusion of data regarding the injections (time and/or amount of injected units) into programmes (apps) designed to assist the user.

Thus, the present invention can provide a protective cap for a device, preferably a delivery system for injection of a substance, said protective cap comprising
- a tip part
- a main cap part
- means for releasably attaching the tip part to the main cap part
- a clip on one of the sides of said main cap part wherein the clip is configured to form a grip unit during use of the delivery system, which grip is arranged to engage with a first hand of a user providing stability to the delivery system during injection, and the main cap part is configured to attach the grip to the delivery system during use.

The present invention can also provide a protective cap for a device, preferably a delivery system for injection of a substance, said protective cap comprising
- a tip part
- a main cap part
- means for releasably attaching the tip part to the main cap part
- a grip unit on at least one of the sides of said main cap part wherein the grip unit is configured to form a grip unit during use of the delivery system, which grip is arranged to engage with a first hand of a user providing stability to the delivery system during injection, and the main cap part is configured to attach the grip to the delivery system during use.

If the grip unit is attached by a hinge or similar means to the main cap part, the grip unit can be folded to rest against the main cap part when not in use and be pivoted to one or more positions of use when the user needs the grip unit to help stabilize the device during use. A hinge can allow the movement/positioning of the grip relatively to the main cap part and/or device around one or more axes.

It is possible that the grip comprises means for changing the shape of the grip from a first rest configuration to a second use configuration. For example, the grip unit in a rest configuration is simply a straight bar and in a second use configuration, the grip unit can form a smooth or rough S or e.g. Z or L shape.

The means for changing shape may comprise one or more bending hinges allowing the grip unit to be shaped into a use configuration before use and be folded back to the rest configuration before storage.

It is also possible that the grip unit is at least partly made of materials which can be moulded into a desired shape by the user.

The tip part can be releasably attached to the main cap part by a thread, click means or bayonet joint which enables the user to easily remove and reattach the tip part to the main part while still ensuring that the tip part is not accidentally detached from the main part.

The two part protective cap can be used as a regular protective cap and attached and released from a device as a single unit as known from a regular protective cap. However, the present invention also allows a tip part of the protective cap to be released alone leaving the main cap part still attached to the device.

If the position of the at least one means for assisting the use of the device is adjustable by positioning means, the means for assisting the use of the device can be arranged to fit a user and/or a specific use situation. For example, the means for assisting the use of the device can be arranged in a way which allows the user to slide the means for assisting use along the longitudinal direction of the protective cap and/or to rotate the assisting means to obtain a desired angle.

In some embodiments the protective cap comprises one or more features on the tip part and/or on the main part arranged to help the user obtain a better grip when handling the tip part and or main part of the protective cap.

The means for assisting the use of the device, for example a grip for an injector, can be arranged to have one or more use positions. For example the grip can be fastened to the main part by a joint allowing rotation around one or more axis for example a first and/or second axis.

In several embodiments the grip can rotate around a first axis perpendicular to the length direction of the device when attached hereto. In use the grip can be rotated towards the end/needle of the injector into a position forming a first angel with respect to the length direction of the device. The first angle can for example be between 30-90, 30-60 or 40-55 degrees in order to provide a good hold preferably with room for at least one finger between grip and device.

In several embodiments the grip can rotate around a second axis parallel to the longitudinal direction of the device allowing the grip to extend in a non-radial direction from the device. A non-radial direction allows the user to have an extra contact point against the device. Not only will one or more of the fingers of the first hand be in contact with the grip, a finger, e.g. the index finger, will also touch the device and thus be able to provide more control and stability. An extra contact point can be especially advantageous if the grip is thin. The second angle can for example be between 30 -90, 30-60 or 40-55 degrees in order to provide a good hold with room for at least one finger between grip and device.

Especially when the grip is straight or has another simple shape the adjusting second angle may be helpful to provide a comfortable grip for the user.

The grip can be flat, rounded and/or have a curved shape in order to match a design of the device or to a provide comfortable grip or simply a grip which is optimized with respect to production considerations such as simple manufacturing process or reduced costs.

In other embodiments as described in PCT/DK2012/050321 a grip is part of an instrument for assisting a user during injection of a substance by a delivery system, said instrument comprising:
- A grip unit
- Means for attaching the grip unit to the delivery system wherein said grip unit is arranged to be held by a first hand of the user while a second hand of the user controls the delivery system. This means that by using the present invention coordination of the two hands during injection is made easier. This is achieved in that the first hand holds the grip, and thereby supports the delivery device during the injection. Hereby, the instrument helps stabilize the delivery device during injection and thus helps keep the delivery device steady even during activation of the delivery device and during the time it takes for the injection to take place.

The grip units as described in PCT/DK2012/050321 can be used as grip in the various embodiments of the protective cap and the grips described in relation to the protective cap can be used as grip units for devices as described in PCT/DK2012/050321.

The various grips described in the present application can be used together with the various means of attaching the grip to a device such as a delivery system.

As described in PCT/DK2012/050321 a grip unit can be attached, either directly to the delivery system (e.g. as an integrated structure of the delivery system) or via a holder, preferably at the end of the delivery system near the needle.

The holder can be as described in PCT/DK2012/050321 or a main cap part as described herein.

If the grip unit is directly attached to the delivery system e.g. by being moulded into the system, simple and reliable embodiments can be achieved.

The means for attaching the grip unit to the delivery system can comprise a holder for receiving the delivery system, i.e. the grip can be attached to the delivery system by a holder in which the delivery system can be inserted.

If the holder and the grip unit is a single unit, it is possible to achieve an instrument which is easy to handle and which provides an advantageous stability of the holder and grip relatively to each other.

Thus preferably the holder can either be permanently attached to the grip unit or be configured to be releasable attached to the grip unit.

Thus in several preferred embodiments the holder comprises retaining parts for receiving the delivery system and fastening the delivery system in a desired position in the holder.

These retaining parts may be arranged to grip at least partly around one or more parts of the delivery system and/or to engage with one or more corresponding parts on the delivery system.

The retaining parts may for example be at least partly circumferential parts e.g. crescent shaped parts gripping at least partly around one or more parts of the injector i.e. delivery system.

Thereby the holder may both be used for attachment of the grip as well as keeping the grip and delivery system fixed relatively to each other.

The grip can be attached to the holder/delivery device by a hinge or similar allowing movement/positioning of the grip around one or more axis thereby e.g. allowing the positioning of the grip in one or more first and/or second angels with respect to a delivery unit or other device.

In another aspect the invention relates to a protective cap for a delivery system, said cap comprising a tip part releasably attached to a main part, wherein the tip part and the main part together form an elongated body with a closed tip end.

In some embodiments, the protective cap further comprises at least one means for assisting the use of the delivery system. In other embodiments, the protective cap comprises two or more means for assisting the use of the delivery system.

Such means for assisting the use of the delivery system may be as described above. Thus means for assisting the use of the delivery system may be selected from the group comprising: a grip on one of the sides of the main part, a light source, a timer, a display, means for visualising the number of injected medicine units, and means for transmission of data.

Thus in some embodiments the protective cap comprises means for transmission of data. These means may be able to communicate wirelessly with a receiving unit. Examples of receiving units include a smartphone or a blood glucose monitoring device. Wireless communication may occur via technologies such as Bluetooth, Bluetooth low energy (BLE), near field communication (NFC), or radio frequency identification (RFID). In a preferred embodiment, wireless communication occurs via Bluetooth low energy (BLE).

Thus the present invention relates to a protective cap comprising two or more means for assisting the use of the delivery system, in any combination. In one embodiment, the protective cap comprises means for transmission of data and a light source. The light source may be such that it enhances visualisation of blood veins in order to facilitate injection. In another embodiment, the protective cap further comprises a grip on one of the sides of the main part of the protective cap and/or a timer and/or means for visualising the number of injected medicine units.

In other embodiments the invention relates to a protective cap comprising a measuring device. The measuring device may be located on the main part or on the tip part of the protective cap. The measuring device may be located on the main part. When the main part consists of an inner and an outer part, the measuring may be located on the inner part or on the outer part of the main part. In some embodiments the measuring device is for measuring blood sugar values, as may be relevant for people diagnosed with diabetes. In some embodiments, the blood measuring device is releasably attached to the main part or to the outer part of the main part. The measuring device may be such that it is able to communicate wirelessly with a receiving unit, such as a smartphone or a Blood Glucose Monitoring Device. Such wireless communication may occur via technologies such as Bluetooth, Bluetooth low energy (BLE), near field communication (NFC), or radio frequency identification (RFID). In a preferred embodiment, wireless communication occurs via Bluetooth low energy (BLE).

In some embodiments, the protective cap may further comprise a blood sampling device, allowing the user to sample his blood.

In another aspect the invention also relates to a system comprising a device and a protective cap as described above. Preferably, the device is a delivery system e.g. an insulin pen.

Many people, including those suffering from conditions such as diabetes, use some form of infusion therapy in order to maintain control of their diseases. To mention an example, a huge number of people use insulin pens (also called injectors) for daily insulin therapy through subcutaneous injection alternatively e.g. syringes with needles can be used. This therapy often requires use of one hand to press together a skin fold and one hand to activate the injector (insulin pen). This maneuver is rather complex and requires a calm and controlled hand movement in order to be carried out conveniently. Especially the fact that the injector is controlled by only one hand is the origin of the problems and inconveniences, which the invention addresses.

Other injection such as subcutaneous, intramuscular, intravenous or intradermal also may benefit from a device providing stability and control of the user's hands and of the injection device during injection. The various embodiments disclosed herein can be used in relation to a range of delivery devices and delivery needs.

Preferably the user is the person needing the injection however in some situations a user can optionally also be imagined to be another person performing the injection.

The problems are reduced by the embodiments of the present invention comprising a grip by establishing a physical link between the user's two hands during use of the delivery system making it possible for both hands to take part in the injection and making it possible to use the body for support during the injection process. The method can be implemented by a protective cap with a grip (assisting means). The very specific details of the protective cap will depend on the delivery system used.

Thus according to the present invention is provided a protective cap where to e.g. a grip as described herein or in PCT/DK2012/050321 can be attached in order to assist the user during injection of a substance.

DESCRIPTION OF THE DRAWINGS

The invention will in the following be described in greater detail with reference to the accompanying drawings. The drawings are exemplary and are not to be construed as limiting to the invention.

FIGS. 3a and 3b show a schematic view of alternative embodiments of a protective cap according to the present invention.

FIGS. 4a and FIG. 4b show a schematic view of alternative embodiments of a protective cap according to the present invention.

FIG. 10a-10d illustrate the two angles $\alpha 1$ and $\alpha 2$.

DETAILED DESCRIPTION OF THE INVENTION

Figure 1:
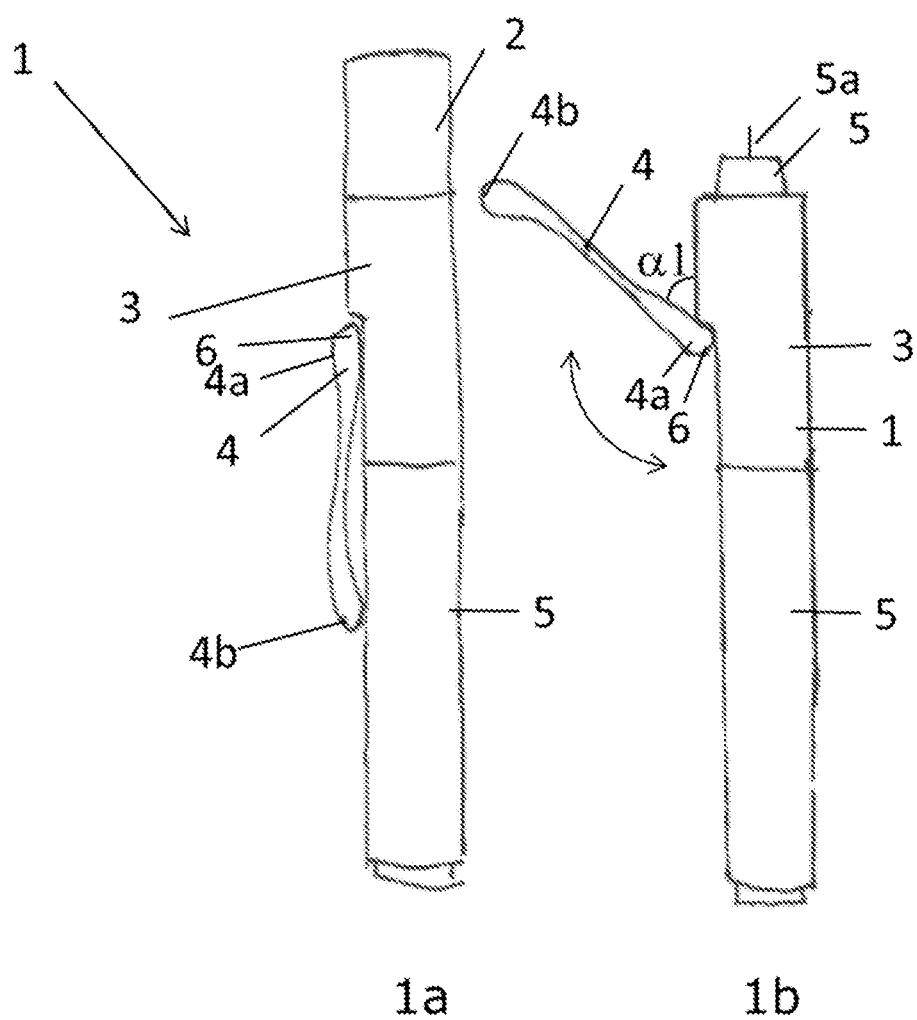
FIGS. 1a and 1b show a schematic view of a protective cap according to the present invention.

FIG. 1a shows a protective cap 1 comprising a tip part 2 and a main part 3. To the main part 3 is attached a means 4 for assisting the use of a device in form of an insulin pen 5.

The means for assisting the user is a grip unit 4 formed by a slightly curved elongated member having a first end 4a and a second end 4b. The grip unit 4 is at its first end 4a attached to the main part by a hinge 6 allowing the grip unit 4 to pivot around its mounting axis.

In FIG. 1b, the means 4 for assisting the use of the device 5 has been pivoted into a position of use where it can be engaged by the first hand of the user while the user activates the delivery system using his second hand. First angle $\alpha 1$ is indicated between the longitudinal direction of the delivery system and the length direction of the grip. Also, the tip part 2 has been released from the main part revealing the needle 5a of the delivery system. If a needle is not attached, the removed tip part will allow access to mount the needle on the delivery system.

Thus, in FIG. 1b the main cap part is used to fasten the at least one means for assisting the use of the delivery system (here in form of grip unit 4) to the delivery system 5 in form of an insulin pen.

The protective cap 1 is substantially formed as a tubular member with an open end opposing a closed end.

The main cap part is substantially a tubular member with a first end 3a and a second end 3b.

The protective cap, when tip part and main part are attached to each other, is arranged to be attached onto a device e.g. a delivery system as showed here to protect the end of the delivery system where the needle 5a is attached or is to be attached. When the tip part is released, and the main part is still attached to the device/delivery system the device can be used as intended and the grip unit attached to the delivery system by the main cap part can be used to stabilize the device.

Figure 2:
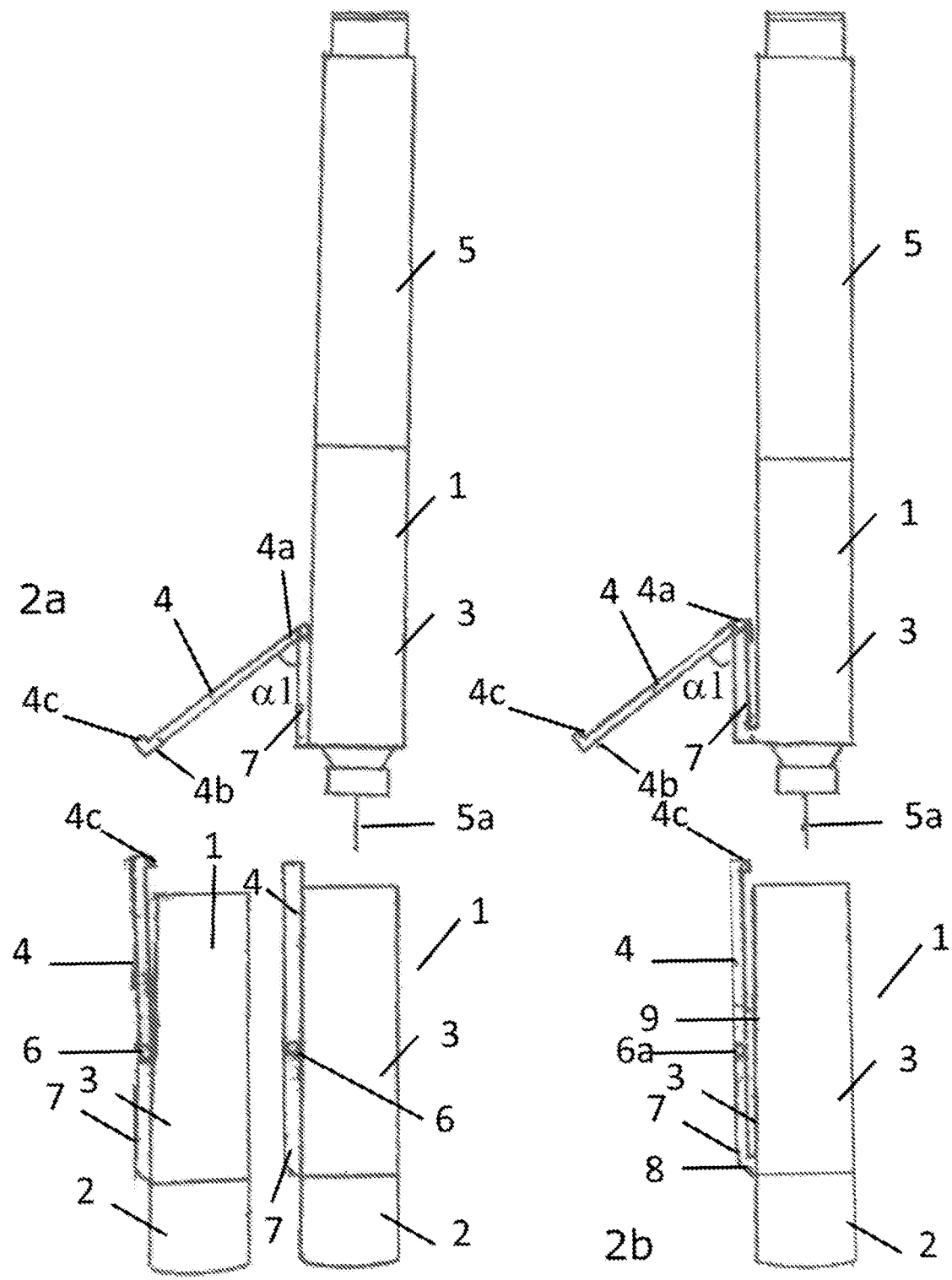
FIGS. 2a and 2b show a schematic view of alternative embodiments of a protective cap according to the present invention.

FIGS. 2a and 2b show different embodiments of protective caps 1 with a grip unit 4 attached to a main part. In both FIGS. 2a and 2b, the grip unit is in the form of a slim elongated bar which at its end furthest away from the point of attachment to the main cap part has a protrusion 4c extending in the direction towards the main cap part.

Both FIGS. 2a and 2b show the main part 3 attached to the delivery system ready for use as well as the protective cap alone with the tip part attached to the main cap part.

In FIG. 2a, the grip unit 4 is attached to the main cap part by a hinge allowing the grip unit to pivot relatively to the main cap part. The main cap part 3 has a ridge 7 which is positioned at the main cap part as an extension of the line of the grip unit 4. In FIG. 2a, the grip unit is attached to the main cap part in a manner which allows the grip unit to be flush against the main cap part when not in use.

FIG. 2b shows a slightly different embodiment but where the basic elements are the same as in the previous figures. The grip unit 4 is a slim elongated bar which at its end furthest away from the point of attachment to the main cap part has a protrusion 4c extending in the direction towards the main cap part. The protrusion may improve the user's control of the grip 4. The difference between FIG. 2a and FIG. 2b is that the grip at its first end 4a is attached to the main cap part 3 by a solid attachment 8 near the second end 3b of the main cap part 3. The grip unit 4 comprises a bending hinge 6a positioned approximately ⅓ of the longitudinal direction of the grip unit away from the attachment 8. The bending hinge 6a l allows the outer ⅔ of the grip unit to pivot into a position of use which allows the user to engage with the grip in order to stabilize the delivery system during use. There is a narrow space 9 between the grip unit 4 and the main cap part 3 in the rest position allowing the grip unit to be used as a clip e.g. to secure the delivery device with the protective cap according to the invention in a jacket pocket (not shown).

FIGS. 3a and 3b show another embodiment of the present invention in its rest position in FIG. 3a and in its position of use in FIG. 3b with the grip unit pivoted into the position of use and the tip cap part removed revealing the needle 5a of the delivery system. In this embodiment, the grip part is slightly curved forming a soft depression 10 which may improve the user's comfort and hold on the grip 4.

FIGS. 4a and 4b show embodiments of the present invention wherein the grip unit 4 comprises a hinge 6 and two bending hinges 6a (FIG. 4a) and three bending hinges 6a (FIG. 4b). In these embodiments, the bending hinges 6a are used as means for changing the shape of the grip unit 4 allowing the grip unit to form a rough S-like shape.

Both FIGS. 4a and 4b show the main part 3 attached to the delivery system ready for use as well as the full protective cap alone with the tip part attached to the main cap part.

Figure 5A:
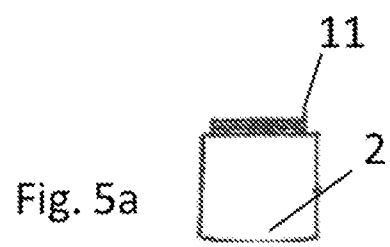
FIGS. 5a and 5b show a schematic view of alternative embodiments of a tip part according to the present invention.
Figure 5B:
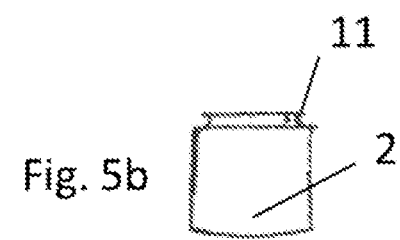

FIG. 5a shows a tip cap part having thread 11 for attaching the tip part to the main cap part. FIG. 5b shows a tip part with a click arrangement 11 allowing the tip part to be attached to the main cap part by a simple click lock.

Figure 6:
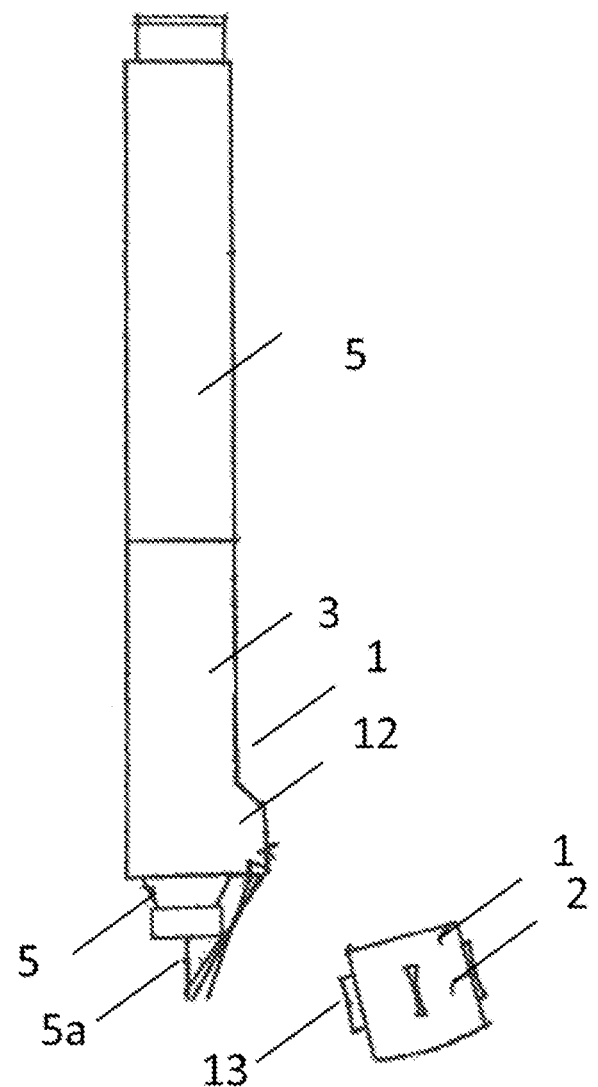
FIG. 6 shows a schematic view of a protective cap with a light source according to the present invention.

FIG. 6 shows a protective cap 1 according to the present invention having a tip part 2 detachable from a main cap part 3. In this embodiment, the at least one means for assisting the use of the delivery system is a light source 12 attached to the main cap part 3. Thus, by the embodiment shown in FIG. 6, the at least one means for assisting the use of the device (the light source) lights up the area of the injection site both prior to and during the injection. The light source can comprise on/off button and means for ensuring an optimal angel of the light.

The light source may also advantageously be attached to e.g. a writing pen thus providing light to an area around the pen.

When the main cap part is connected to the delivery system 5 and the tip cap part is released, the needle 5a is free and ready for use. In this configuration, the user can use the light source 12 to assist the use of the delivery system by improving the lighting conditions at the injection site significantly.

In FIG. 6, the tip cap part is arranged with a number of elongated protrusions 13 which can improve the user's hold on the tip part when releasing and attaching it to the main cap part. The main cap part can be arranged with means of a similar function however in many embodiments, the at least one means for assisting the use of the delivery system attached to the main cap part may provide an improved hold for the user.

Figure 7:
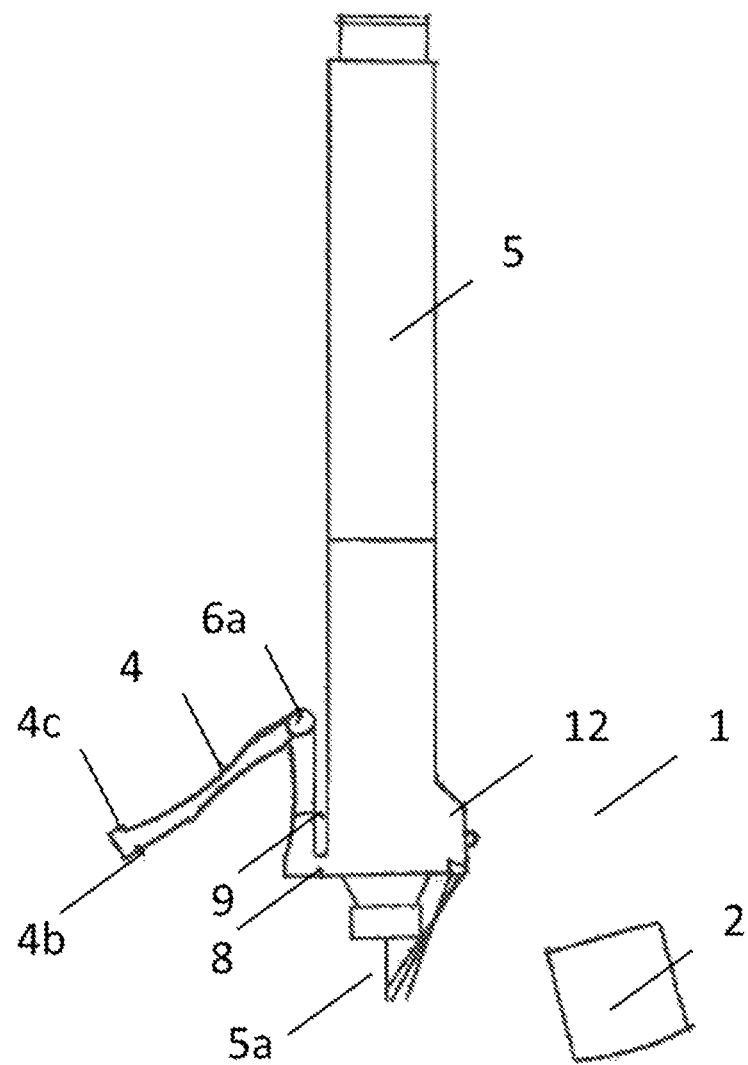
FIG. 7 shows a schematic view of a protective cap with a light source and a grip unit according to the present invention.

FIG. 7 shows a delivery system with two means for assisting the use of the delivery system—a grip unit 4 and a light source 12—attached by the main cap part 3.

Figure 8A:
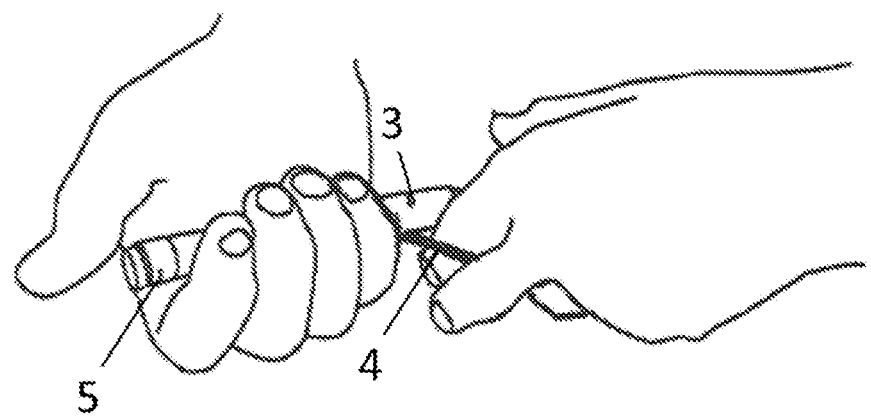
FIGS. 8a and 8b show a schematic view of the use of a protective cap with a grip unit according to the present invention.
Figure 8B:
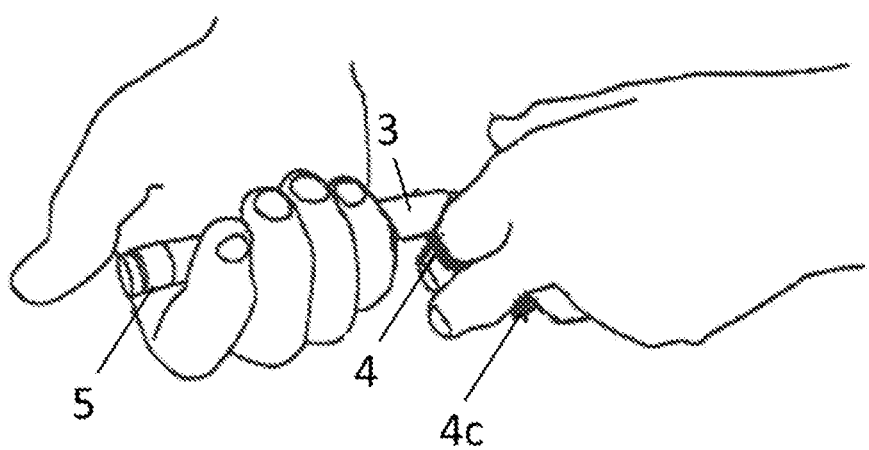

FIGS. 8a and 8b show a grip unit 4 on a protective cap 1 attached to a delivery system 5 in use. The user engages the grip unit with a first hand and holds and actives the delivery system by a second hand 15.

In these figures, it is seen how the shape and arrangement of the grip unit enables the user to engage with the grip and still being able to move the fingers of the first hand sufficiently to create a skin fold as often required when performing an insulin injection.

Figure 9C:
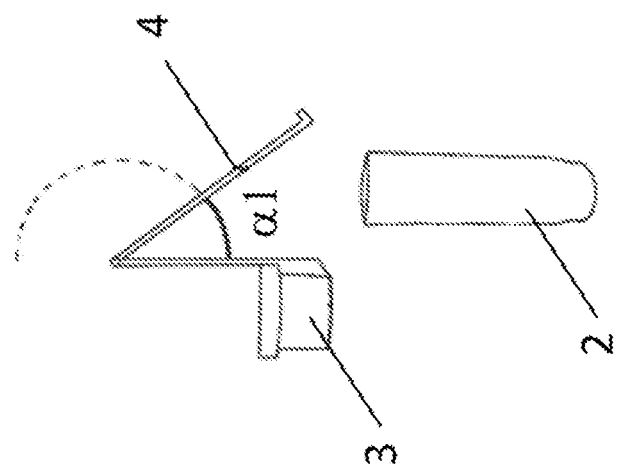
FIGS. 9a, 9b and 9c show a protective cap according to the present invention for a syringe.
Figure 9B:
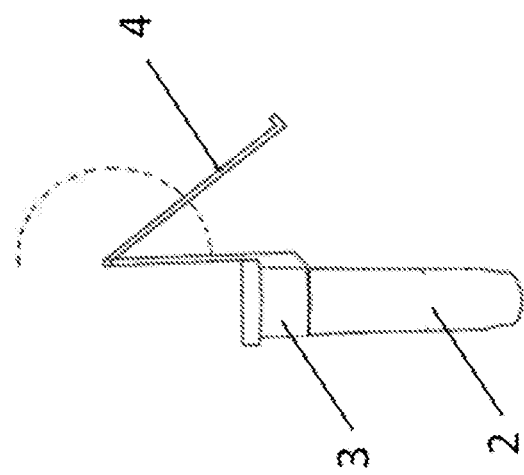
Figure 9A:
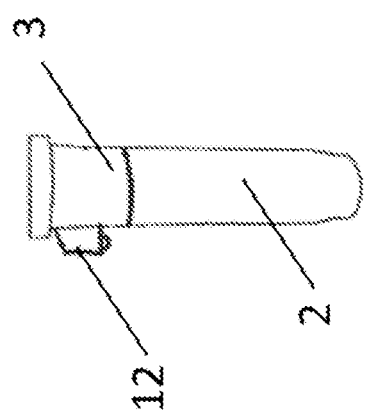

FIG. 9a-9c shows a protective cap 1 having a main cap part 3 and a tip part 2 suited for use with e.g. a syringe.

FIG. 9a shows a protective cap 1 having a main cap part 3 and a tip part 2 suited for use with e.g. a syringe further comprising a light source 12 as the assisting means.

FIG. 9b shows a protective cap 1 having a main cap part 3 and a tip part 2 suited for use with e.g. a syringe having a grip 4 as the assisting means.

FIG. 9c shows the protective cap of FIG. 10b where the tip part is released from the main part 3.

FIG. 10a shows a delivery system with indication of the longitudinal direction L and a parallel second axis A2. The figure also shows first axis A1 perpendicular to L and A2 as well as an indication of the first angle $\alpha 1$ between length direction of the grip and length direction L of the injection device.

FIG. 10b shows the delivery system of FIG. 10a taken along the section Xb-Xb wherein the grip 4 extends in a radial manner from the delivery system i.e. where the second angle $\alpha 2$ is 90°.

FIG. 10c shows a delivery system similar to that of FIG. 10a wherein the grip extends in a non-radial manner from the delivery system in the present example the second angle $\alpha 2$ is approximately 50°.

FIG. 10d shows how the non-radial grip allows the finger to rest against the delivery system at a point P away from where the grip is attached to the delivery system opposed to the situation with the radial grip shown in FIG. 10b.

Figure 11A:
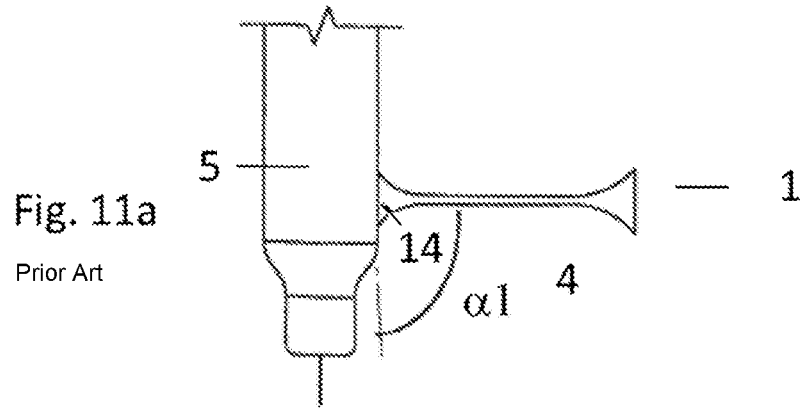
FIGS. 11a and 11b show two different grips.
Figure 11B:
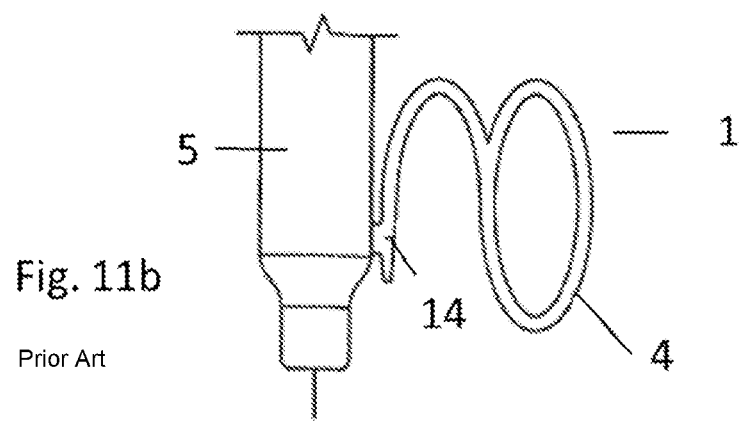

FIGS. 11a and 11b, show and the following FIGS. 12 and 13 shows embodiments of grip unit and holder as known from PCT/DK2012/050321. The grips can be used in various embodiments of the present invention e.g. as grip of a protective cap.

FIGS. 11a and 11b, show two alternative embodiments of a grip unit 4. FIG. 11a shows a grip unit 4 which extends perpendicular or substantially perpendicular to the delivery system 5 to which it is attached by attachment means 14. The shape of the grip unit 4 is basically a slightly curved bar. This embodiment offers a very simple solution to which comfort and/or improved grip may be provided by adjusting the curvature of the grip.

The attachment means 14 can comprise a first and second lock part and may either attached the grip unit 4 releasable to the delivery system or the attachment means 14 may form a permanent attachment between grip unit 4 and delivery system 5. In either case the attachment means may form a rigid coupling fixing the grip unit 4 and delivery system with respect to each other. Alternatively the attachment means may form an at least partly flexible attachment making it possible to adjust e.g. the angle $\alpha 1$ and/or $\alpha 2$ between delivery system 5 and grip unit 4.

FIG. 11b shows an embodiment of a grip unit which comprises a semicircular first grip part and a circular second grip part. The grip unit of FIG. 11b is attached to the delivery system 5 by attachment means 14 as described herein.

The grip units of FIGS. 11a and 11b may be attached directly to the injector 5 or may releasable or permanently attached to a holder such as a main cap part or as described in the following figures.

Figure 12A:
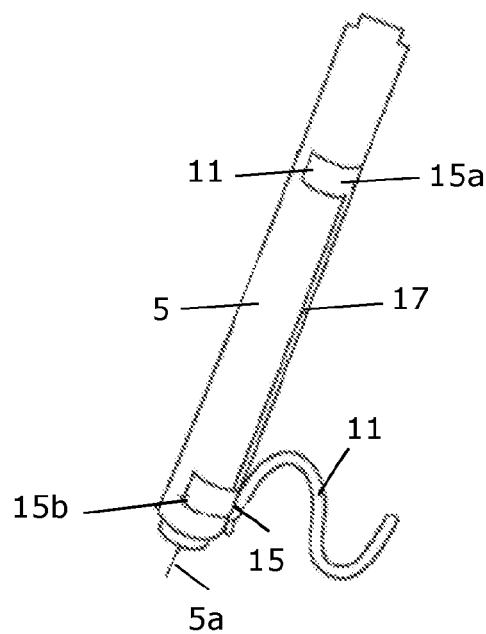
FIGS. 12a and 12b show alternative means for attaching a grip to a delivery system.

FIG. 12a shows an embodiment of the holder 9 of the instrument 1. The holder 15 comprises an upper 15a and a lower 15b crescent shaped element 16 partly encircling the delivery system 2 connected by a bar 17. The grip unit 4 is attached at or near the lower crescent shaped element 15b. The attachment of the grip unit to the holder 4 may be permanent or releasable. If the crescent shaped elements and the bar is made of e.g. thin materials the holder may add very little weight to the delivery system as well as it may be arranged to fit smoothly to the delivery system. This may make it possible to keep the holder attached to the delivery system after use if desired and detached the grip unit alone after use to store separately or together with the delivery system.

Figure 12B:
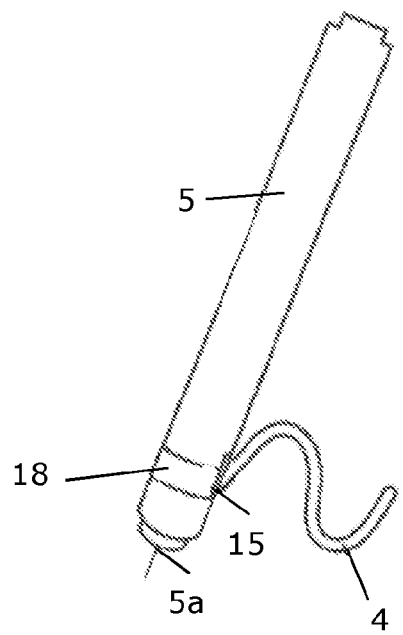

FIG. 12b shows yet another embodiment of a holder according to the present invention. Here the holder simply forms a tight band 18 around a part of the delivery system 2 near the needle. The grip unit 4 may be permanently or releasable attached to the holder.

As above the grip unit 4 of FIGS. 12a and 12b is attached to the holder by attachment means which are further discussed above under FIG. 10a.

Figure 13A:
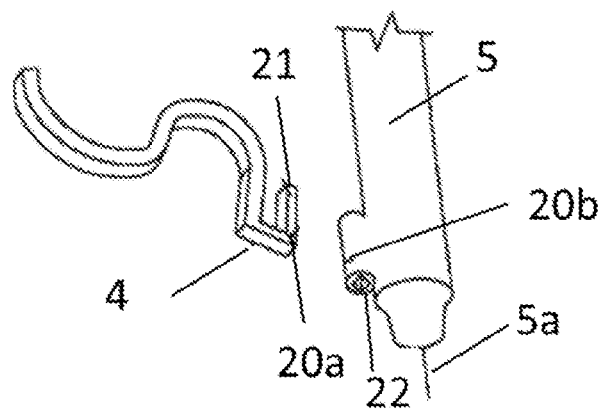
FIGS. 13a and 13b show further alternative means for attaching a grip to a delivery system.

FIG. 13a shows an embodiment of first 20a and second 20b lock part. In this case the first lock part is a bar 21 which is arranged to engage in the second lock part in form of a bore 22 on the delivery system (or alternatively on a holder). The bore 22 is located in a part contained in the delivery system.

The bar 21 and bore 22 may be shaped to match each other in different ways in order to allow fixation of the grip unit 5 at one or more angels with respect to the delivery system 5. In the present example the bore and bar have a square cross section but may have various other cross sections such as e.g. an octagon which will allow the grip and delivery system to be fixed with respect to each other in various angles.

Figure 13B:
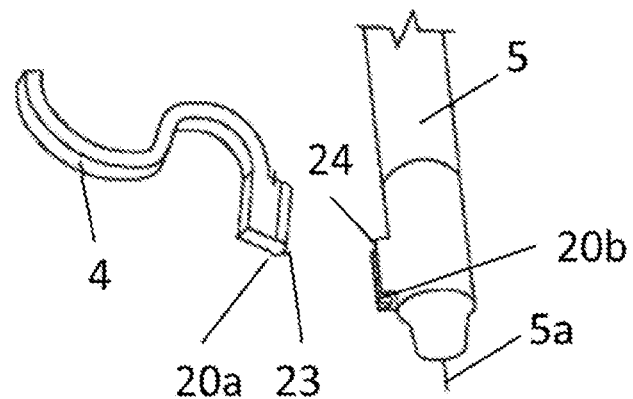

FIG. 13b shows yet another embodiment of attachment means comprising a first 20a and second 20b lock part. In this embodiment the first lock part of the grip unit 4 is a semicircular bar 23 arranged to slide into second lock part 20b of the delivery system in for of a groove 24. The semicircular bar 23 may have a collar which prevents the first lock part 20a of sliding too far into the second lock part 20b i.e. groove 24. In the present embodiment the first and second lock part are arranged to form a tight grip which is stabile but may provide the option of correcting the angle between delivery system and grip unit 4 if desired without compromising the stability of the instrument during use.

Figure 14A:
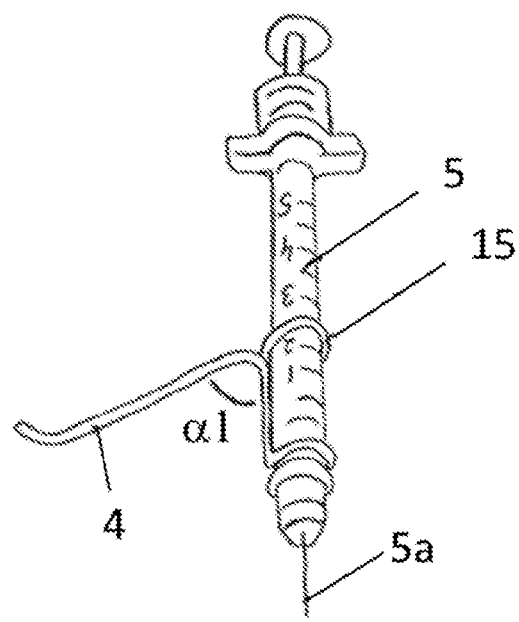
FIGS. 14a and 14b show means for attaching an alternative grip to a delivery system.

FIG. 14a shows a grip 4 attached to a delivery system in form of a syringe by a holder 15 which can be slid or clicked onto the delivery system. Here the grip is an L shaped element extending from the delivery system with an angle α1 of approximately 40 to 60°. The grip as well as the other grips described herein can be used with various delivery systems including e.g. syringes and/or injector pens.

Figure 14B:
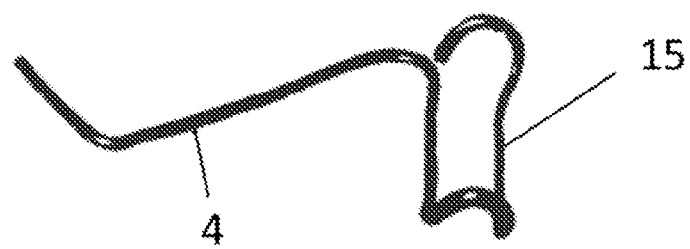

FIG. 14b shows the grip and holder from FIG. 14a disengaged from the delivery system.

Figure 15:
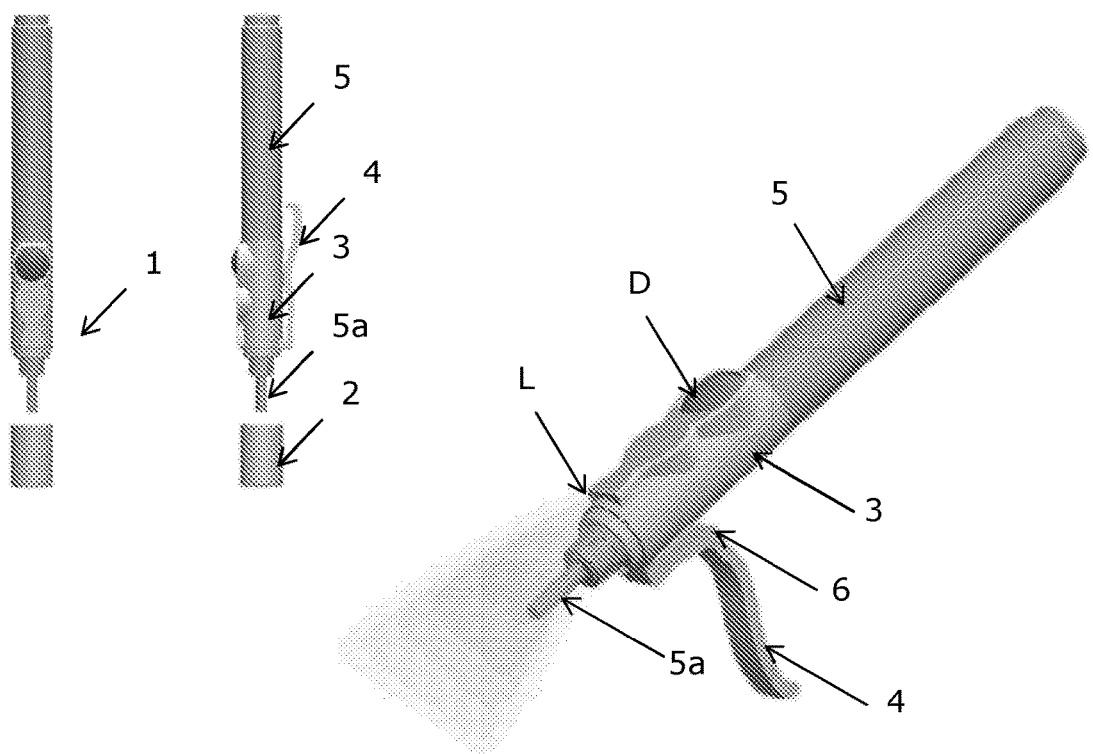
FIG. 15 shows different views of one embodiment of the invention.

FIG. 15 shows three views of a protective cap 1 according to the invention, comprising a light source L, a grip 4 and a display D.

Figure 16:
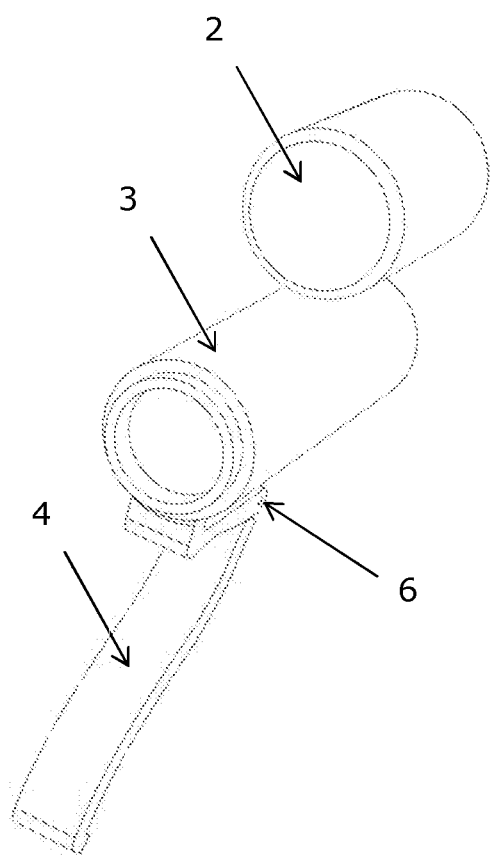
FIGS. 16a-16c show different views of a protective cap according to the invention.

FIG. 16a shows a protective cap comprising a grip 4 with a hinge 6 on one of the sides of the main part 3.

FIGS. 16b and 16c show the same protective cap where the tip part is released from the main part, in two different views.

Figure 17:
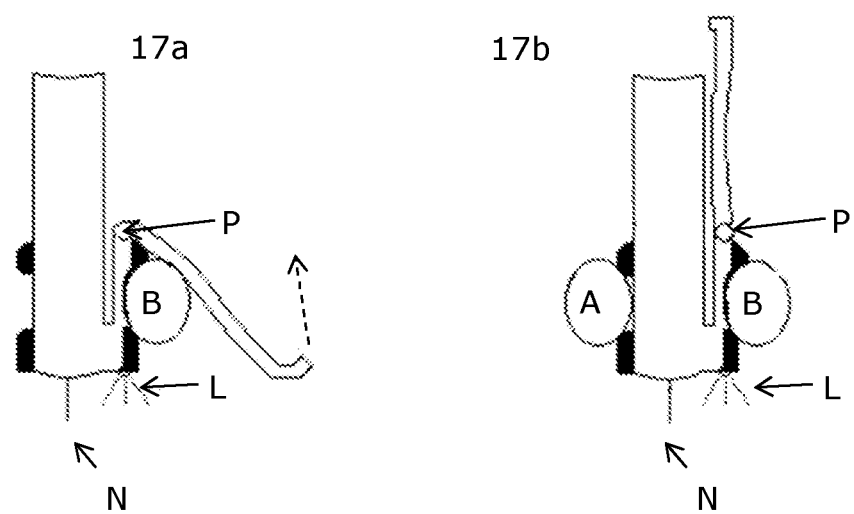
FIGS. 17a-17b show two embodiments of the invention.

FIGS. 17a and 17b show two different embodiments of the main part of a protective cap according to the invention. FIG. 17a shows a main part comprising 4 recesses (in black), an O-ring B and a clip, which may rotate around the pivot point P, as indicated by the hashed arrow. Two of the recesses are located on the clip. The main part further comprises a light L. FIG. 17b shows a main part comprising 4 recesses (in black), two O-rings A and B and a clip, which may rotate around the pivot point P, as indicated by the hashed arrow. Two of the recesses are located on the clip. The main part further comprises a light L. N: needle.

Figure 18:
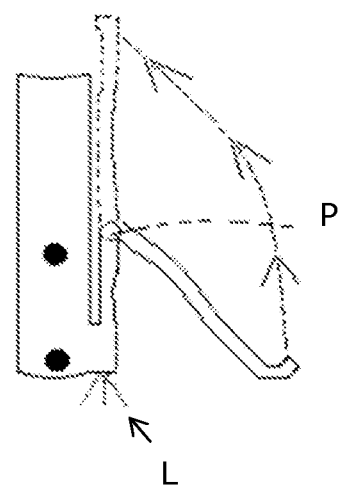
FIG. 18 shows an embodiment of the invention.

FIG. 18 shows another embodiment of the main part of a protective cap according to the invention. The main part comprises a clip unit and 4 recesses (only 2 are shown, in black), where the recesses are not located on the clip. The clip unit may rotate around the pivot P, as indicated by the arrows. The embodiment shown further comprises a light L.

Figure 19:
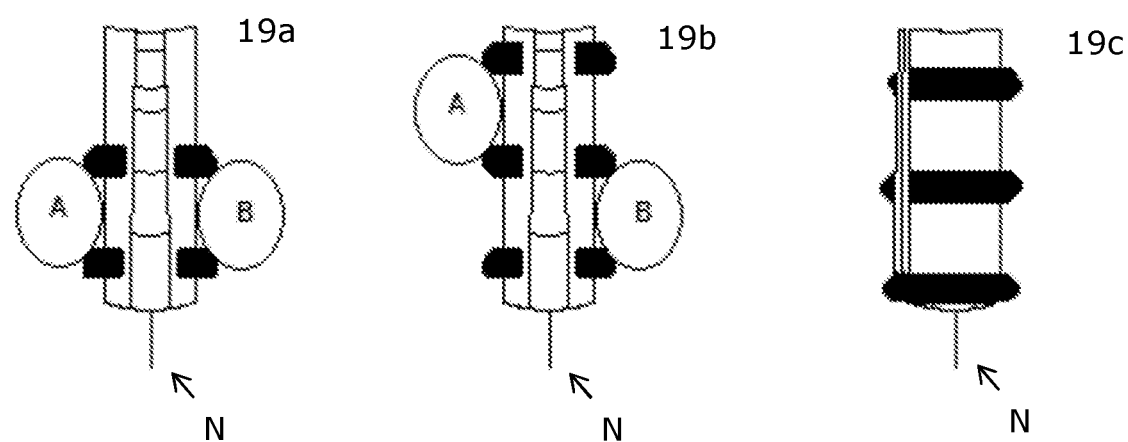
FIG. 19a-19c show three embodiments of the invention.

FIG. 19a-19c show three embodiments of the invention. FIG. 19a shows an embodiment with 2 pairs of recesses (in black) and two O-rings A and B arranged symmetrically on the sides of the main part. FIG. 19b shows an embodiment with 3 pairs of recesses (in black) and two O-rings A and B arranged on the sides of the main part, but on different axes. FIG. 19c shows an embodiment with one circular recess and two partly circular recesses. N: needle.

Figure 20:
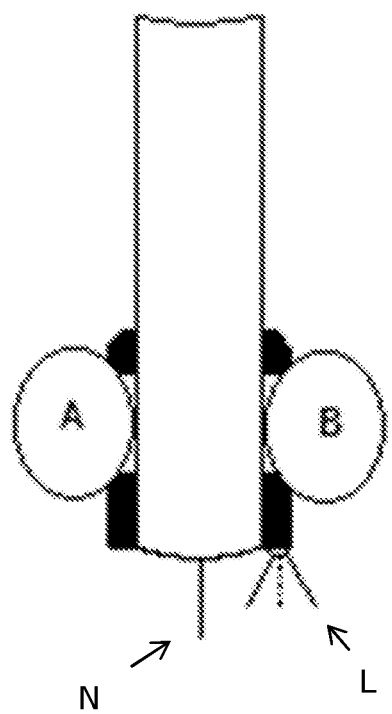
FIG. 20 shows an embodiment of the invention.

FIG. 20 shows an embodiment of a main part of the protective cap according to the invention. The main part comprises 2 pairs of recesses and two O-rings A and B arranged symmetrically on the main part, as well as a light L. N: needle.

The invention claimed is:

1. A releasable protective cap for the protection of a container part of an injection pen with an elongated, substantially tubular body for delivering a medical substance through a needle attached or to be attached to said injection pen, said releasable protective cap is configured to only partly cover said injection pen, said releasable protective cap further characterized in that:
   said releasable protective cap is shaped to cover all of said container part of said injection pen;
   said releasable protective cap comprises a tip part directly releasably attached to a main part; an outer surface including means for releasably attaching said tip part to said main part;
   said tip part and said main part together form an elongated, substantially tubular body with a closed tip end;
   said releasable protective cap comprises at least one selected from the group of a grip unit on an outside of said main part, a recess on the outside of said main part, a battery, an outward directed light source, a timer, a display, a measuring device, a blood sampling device, and a data transmitter,
   said releasable protective cap is arranged to be releasably attached to said injection pen by said main part which is releasable from said injection pen;
thereby enabling the addition of the needle to said injection pen both when said tip part is detached from said main part while the entire main part is attached to said injection pen, and when said tip part and said main part both are detached from said injection pen, thereby enabling the delivery of the medical substance through said needle by the use of said injection pen in combination with said releasable protective cap.

2. The releasable protective cap according to claim 1 comprising the timer, wherein said timer is arranged to show a time elapsed since a last injection.

3. The releasable protective cap according to claim 1 or 2 comprising a timer, wherein said time is automatically activated when said tip part and said main part of the releasable protective cap are separated.

4. The releasable protective cap according to claim 3 comprising the timer, wherein said timer is automatically activated when said tip part and said main part are separated for a time interval greater than a specific duration.

5. The releasable protective cap according to claim 1, 2, 3 or 4 comprising the timer, further comprising a button for resetting said timer to a previous value.

6. The releasable protective cap according to claim 1 comprising the data transmitter, wherein said data transmitter transmits a time since a last injection and/or a number of injected medicine units and wherein said data transmitter can communicate wirelessly with a receiving unit.

7. The releasable protective cap according to claim 6, wherein the wireless communication happens via Bluetooth, Bluetooth low energy (BLE), near field communication (NFC) or radio frequency identification (NFC).

8. The releasable protective cap according to claim 6 or 7, wherein the receiving unit is a smartphone and/or a Blood Glucose Monitoring Device.

9. The releasable protective cap according to claim 1 comprising the outward directed light source, wherein the light source allows visualization of veins under a surface of a skin when an injection takes place.

10. The releasable protective cap according to claim 9, wherein the light source is a white, a blue, a red or near infrared light source.

11. The releasable protective cap according to claim 1 comprising the display, wherein the display is arranged to visualize a number of injected medicine units.

12. The releasable protective cap according to claim 1 comprising the measuring device, wherein the measuring device is for measuring blood sugar values.

13. The releasable protective cap according to claim 1 comprising the data transmitter, wherein the data transmitter is arranged to communicate wirelessly with a receiving unit.

14. A system comprising the injection pen and the releasable protective cap according to any of claim 1, 2, 3, 4, 5, 6, and 8-9.

15. The system according to claim 14, wherein the injection pen is an insulin pen.

* * * * *